(12) United States Patent
Wudyka (10) Patent No.: US 9,155,821 B2
(45) Date of Patent: Oct. 13, 2015

(54) FLUID COLLECTION CANISTER INCLUDING CANISTER TOP WITH FILTER MEMBRANE AND NEGATIVE PRESSURE WOUND THERAPY SYSTEMS INCLUDING SAME

(71) Applicant: Smith & Nephew, Inc., Memphis, TN (US)

(72) Inventor: Scott Wudyka, Marlborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 127 days.

(21) Appl. No.: 14/031,384

(22) Filed: Sep. 19, 2013

(65) Prior Publication Data

US 2014/0107598 A1 Apr. 17, 2014

Related U.S. Application Data

(63) Continuation of application No. 12/671,995, filed as application No. PCT/US2009/047137 on Jun. 12, 2009, now abandoned, which is a continuation-in-part of application No. 12/481,617, filed on Jun. 10, 2009, now abandoned.

(51) Int. Cl.
*A61M 1/00* (2006.01)
*A61M 27/00* (2006.01)

(52) U.S. Cl.
CPC ........... *A61M 1/0031* (2013.01); *A61M 1/0001* (2013.01); *A61M 1/0049* (2013.01);
(Continued)

(58) Field of Classification Search
CPC .................... A61M 1/0001; A61M 2205/7536

USPC ........................................................ 604/319
See application file for complete search history.

(56) References Cited

U.S. PATENT DOCUMENTS 3,026,874 A 3/1962 Stevens
3,367,332 A 2/1968 Groves
(Continued)

FOREIGN PATENT DOCUMENTS

DE 41 11 122 A1 4/1993
DE 43 06 478 9/1994
(Continued)

OTHER PUBLICATIONS

International Search Report for PCT/US09/047137, dated Aug. 7, 2009.
(Continued)

*Primary Examiner* — Susan Su
(74) *Attorney, Agent, or Firm* — Knobbe, Martens, Olson & Bear, LLP (57) ABSTRACT

A fluid collection canister including a chamber to collect fluids and a canister top disposed over the chamber. The canister top includes a bottom side facing into the chamber, including first and second ribs disposed thereon, a filter membrane attached to the first and second ribs, a first port to communicate with the chamber and a pressure source external to the chamber, and a second port to communicate with the chamber and a sensor external to the chamber. The first port is in fluid communication with a first area, which is bounded by the filter membrane, the first and second ribs and the bottom side of the canister top. The second port is in fluid communication with a second area, which is bounded by the filter membrane, the second rib and the bottom side of the canister top.

8 Claims, 7 Drawing Sheets

(52) U.S. Cl.
CPC ............. *A61M1/0088* (2013.01); *A61M 27/00* (2013.01); *A61M 2205/18* (2013.01); *A61M 2205/3317* (2013.01); *A61M 2205/3331* (2013.01); *A61M 2205/3382* (2013.01); *A61M 2205/7536* (2013.01)

(56) References Cited

U.S. PATENT DOCUMENTS

| | | | |
|---|---|---|---|
| 3,486,504 A | 12/1969 | Austin, Jr. | |
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 3,980,166 A | 9/1976 | DeFeudis | |
| 4,063,556 A | 12/1977 | Thomas et al. | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,202,331 A | 5/1980 | Yale | |
| 4,224,945 A | 9/1980 | Cohen | |
| 4,228,798 A | 10/1980 | Deaton | |
| 4,266,545 A | 5/1981 | Moss | |
| 4,280,680 A | 7/1981 | Payne | |
| 4,382,441 A | 5/1983 | Svedman | |
| 4,510,802 A | 4/1985 | Peters | |
| 4,524,064 A | 6/1985 | Nambu | |
| 4,538,645 A | 9/1985 | Perach | |
| 4,655,754 A * | 4/1987 | Richmond et al. ............ | 604/323 |
| 4,700,479 A | 10/1987 | Saito et al. | |
| 4,710,165 A | 12/1987 | McNeil et al. | |
| 4,738,257 A | 4/1988 | Meyer et al. | |
| 4,743,232 A | 5/1988 | Kruger | |
| 4,870,975 A | 10/1989 | Cronk et al. | |
| 4,874,363 A | 10/1989 | Abell | |
| 4,969,880 A | 11/1990 | Zamierowski | |
| 4,990,137 A | 2/1991 | Graham | |
| 4,997,438 A | 3/1991 | Nipper | |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,135,485 A | 8/1992 | Cohen et al. | |
| 5,141,503 A | 8/1992 | Sewell, Jr. | |
| 5,149,331 A | 9/1992 | Ferdman et al. | |
| 5,152,757 A | 10/1992 | Eriksson | |
| 5,160,322 A | 11/1992 | Scheremet et al. | |
| 5,176,663 A | 1/1993 | Svedman et al. | |
| 5,178,157 A | 1/1993 | Fanlo | |
| 5,180,375 A | 1/1993 | Feibus | |
| 5,195,977 A | 3/1993 | Pollitt | |
| 5,261,893 A | 11/1993 | Zamierowski | |
| 5,263,922 A | 11/1993 | Sova et al. | |
| D364,679 S | 11/1995 | Heaton et al. | |
| 5,484,427 A | 1/1996 | Gibbons | |
| 5,527,293 A | 6/1996 | Zamierowski | |
| 5,536,233 A | 7/1996 | Khouri | |
| 5,549,584 A | 8/1996 | Gross | |
| 5,588,958 A | 12/1996 | Cunningham et al. | |
| 5,624,374 A | 4/1997 | Von Iderstein | |
| 5,636,643 A | 6/1997 | Argenta et al. | |
| 5,645,081 A | 7/1997 | Argenta et al. | |
| 5,678,564 A | 10/1997 | Lawrence et al. | |
| 5,701,917 A | 12/1997 | Khouri | |
| 5,733,305 A | 3/1998 | Fleischmann | |
| 5,779,657 A | 7/1998 | Daneshvar | |
| 5,807,359 A * | 9/1998 | Bemis et al. ................. | 604/322 |
| 5,840,049 A | 11/1998 | Tumey et al. | |
| 5,911,222 A | 6/1999 | Lawrence et al. | |
| 5,944,703 A | 8/1999 | Dixon et al. | |
| 5,960,837 A | 10/1999 | Cude | |
| 6,010,524 A | 1/2000 | Fleischmann | |
| 6,071,267 A | 6/2000 | Zamierowski | |
| 6,117,111 A | 9/2000 | Fleischmann | |
| 6,135,116 A | 10/2000 | Vogel et al. | |

| | | | |
|---|---|---|---|
| D434,150 S | 11/2000 | Turney et al. | |
| 6,142,982 A | 11/2000 | Hunt et al. | |
| 6,174,306 B1 | 1/2001 | Fleischmann | |
| 6,203,563 B1 | 3/2001 | Fernandez | |
| 6,261,276 B1 | 7/2001 | Reitsma | |
| 6,325,788 B1 | 12/2001 | McKay | |
| 6,345,623 B1 | 2/2002 | Heaton et al. | |
| 6,348,423 B1 | 2/2002 | Griffiths et al. | |
| 6,395,955 B1 | 5/2002 | Roe et al. | |
| 6,398,767 B1 | 6/2002 | Fleischmann | |
| 6,406,447 B1 | 6/2002 | Thrash et al. | |
| 6,420,622 B1 | 7/2002 | Johnston et al. | |
| 6,458,109 B1 | 10/2002 | Henley et al. | |
| 6,488,643 B1 | 12/2002 | Tumey et al. | |
| 6,500,112 B1 | 12/2002 | Khouri | |
| D469,175 S | 1/2003 | Hall et al. | |
| D469,176 S | 1/2003 | Hall et al. | |
| 6,520,982 B1 | 2/2003 | Boynton et al. | |
| 6,547,255 B1 | 4/2003 | Donaway et al. | |
| 6,553,998 B2 | 4/2003 | Heaton et al. | |
| D475,134 S | 5/2003 | Randolph | |
| 6,557,704 B1 | 5/2003 | Randolph | |
| D478,659 S | 8/2003 | Hall et al. | |
| 6,607,495 B1 | 8/2003 | Skalak et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| D488,558 S | 4/2004 | Hall | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,855,860 B2 | 2/2005 | Ruszczak et al. | |
| 6,856,821 B2 | 2/2005 | Johnson | |
| 6,887,228 B2 | 5/2005 | McKay | |
| 6,887,263 B2 | 5/2005 | Bleam et al. | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,960,181 B2 | 11/2005 | Stevens | |
| 6,979,324 B2 | 12/2005 | Bybordi et al. | |
| 6,994,702 B1 | 2/2006 | Johnson | |
| 7,022,113 B2 | 4/2006 | Lockwood et al. | |
| 7,037,254 B2 | 5/2006 | O'Connor et al. | |
| 7,052,167 B2 | 5/2006 | Vanderschuit | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,719 B2 | 10/2006 | Rosenberg | |
| 7,128,735 B2 | 10/2006 | Weston | |
| 7,144,390 B1 | 12/2006 | Hanningan et al. | |
| 7,153,294 B1 * | 12/2006 | Farrow .......................... | 604/319 |
| 7,169,151 B1 | 1/2007 | Lytinas | |
| 7,182,758 B2 | 2/2007 | McCraw | |
| 7,195,624 B2 | 3/2007 | Lockwood et al. | |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| D544,092 S | 6/2007 | Lewis | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| D565,177 S | 3/2008 | Locke et al. | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,396,345 B2 | 7/2008 | Knighton et al. | |
| 7,410,495 B2 | 8/2008 | Zamierowski | |

(56) References Cited

U.S. PATENT DOCUMENTS

| | | | |
|---|---|---|---|
| 7,413,570 | B2 | 8/2008 | Zamierowski |
| 7,413,571 | B2 | 8/2008 | Zamierowski |
| 7,422,576 | B2 | 9/2008 | Boynton et al. |
| 7,569,742 | B2 | 8/2009 | Haggstrom et al. |
| 7,625,362 | B2 | 12/2009 | Boehringer et al. |
| 7,699,823 | B2 | 4/2010 | Haggstrom et al. |
| 7,846,141 | B2 | 12/2010 | Weston |
| 7,909,805 | B2 | 3/2011 | Weston |
| 8,267,909 | B2 * | 9/2012 | Clementi et al. ............ 604/320 |
| 2001/0020145 | A1 | 9/2001 | Satterfield |
| 2001/0031943 | A1 | 10/2001 | Urie |
| 2001/0043943 | A1 | 11/2001 | Coffey |
| 2002/0016577 | A1 | 2/2002 | Ohmstede |
| 2002/0108614 | A1 | 8/2002 | Schultz |
| 2002/0143286 | A1 | 10/2002 | Tumey |
| 2002/0151836 | A1 | 10/2002 | Burden |
| 2002/0161346 | A1 | 10/2002 | Lockwood et al. |
| 2002/0198504 | A1 * | 12/2002 | Risk et al. ............ 604/318 |
| 2003/0078532 | A1 | 4/2003 | Ruszczak et al. |
| 2003/0093041 | A1 | 5/2003 | Risk, Jr. et al. |
| 2003/0181850 | A1 | 9/2003 | Diamond et al. |
| 2003/0208149 | A1 | 11/2003 | Coffey |
| 2003/0212357 | A1 | 11/2003 | Pace |
| 2003/0212359 | A1 | 11/2003 | Butler |
| 2003/0219469 | A1 | 11/2003 | Johnson et al. |
| 2004/0006319 | A1 | 1/2004 | Lina et al. |
| 2004/0030304 | A1 | 2/2004 | Hunt et al. |
| 2004/0039415 | A1 | 2/2004 | Zamierowski |
| 2004/0064111 | A1 | 4/2004 | Lockwood et al. |
| 2004/0064132 | A1 | 4/2004 | Boehringer |
| 2004/0093026 | A1 | 5/2004 | Weidenhagen et al. |
| 2004/0113309 | A1 | 6/2004 | Thompson, Jr. et al. |
| 2004/0122434 | A1 | 6/2004 | Argenta et al. |
| 2004/0167482 | A1 | 8/2004 | Watson |
| 2004/0193218 | A1 | 9/2004 | Butler |
| 2004/0241213 | A1 | 12/2004 | Bray |
| 2004/0243073 | A1 | 12/2004 | Lockwood et al. |
| 2004/0249353 | A1 | 12/2004 | Risks, Jr. et al. |
| 2004/0260230 | A1 | 12/2004 | Randolph |
| 2005/0004534 | A1 | 1/2005 | Lockwood et al. |
| 2005/0010153 | A1 | 1/2005 | Lockwood et al. |
| 2005/0020955 | A1 | 1/2005 | Sanders et al. |
| 2005/0070835 | A1 | 3/2005 | Joshi |
| 2005/0070858 | A1 | 3/2005 | Lockwood et al. |
| 2005/0085795 | A1 | 4/2005 | Lockwood et al. |
| 2005/0090787 | A1 | 4/2005 | Risk, Jr. et al. |
| 2005/0101940 | A1 | 5/2005 | Radl et al. |
| 2005/0107756 | A1 | 5/2005 | McCraw |
| 2005/0131327 | A1 | 6/2005 | Lockwood et al. |
| 2005/0137539 | A1 | 6/2005 | Biggie et al. |
| 2005/0147562 | A1 | 7/2005 | Hunter et al. |
| 2005/0177190 | A1 | 8/2005 | Zamierowski |
| 2005/0182445 | A1 | 8/2005 | Zamierowski |
| 2005/0222527 | A1 | 10/2005 | Miller et al. |
| 2005/0261615 | A1 | 11/2005 | Weston |
| 2005/0261642 | A1 | 11/2005 | Weston |
| 2005/0261643 | A1 | 11/2005 | Bybordi et al. |
| 2006/0015087 | A1 | 1/2006 | Risk, Jr. et al. |
| 2006/0029650 | A1 | 2/2006 | Coffey |
| 2006/0039742 | A1 | 2/2006 | Cable, Jr. et al. |
| 2006/0041247 | A1 | 2/2006 | Petrosenko et al. |
| 2006/0079852 | A1 | 4/2006 | Bubb et al. |
| 2006/0100586 | A1 | 5/2006 | Karpowicz et al. |
| 2006/0100594 | A1 | 5/2006 | Adams et al. |
| 2006/0116620 | A1 | 6/2006 | Oyaski |
| 2006/0149170 | A1 | 7/2006 | Boynton et al. |
| 2007/0005028 | A1 | 1/2007 | Risk, Jr. et al. |
| 2007/0014837 | A1 | 1/2007 | Johnson et al. |
| 2007/0016152 | A1 | 1/2007 | Karpowicz |
| 2007/0021697 | A1 | 1/2007 | Ginther et al. |
| 2007/0027414 | A1 | 2/2007 | Hoffman et al. |
| 2007/0032754 | A1 | 2/2007 | Walsh |
| 2007/0032755 | A1 | 2/2007 | Walsh |
| 2007/0032778 | A1 | 2/2007 | Heaton et al. |
| 2007/0055209 | A1 | 3/2007 | Patel et al. |
| 2007/0078432 | A1 | 4/2007 | Halseth et al. |
| 2007/0135779 | A1 | 6/2007 | Lalomia et al. |
| 2007/0167927 | A1 | 7/2007 | Hunt et al. |
| 2007/0179460 | A1 | 8/2007 | Adahan |
| 2007/0185426 | A1 | 8/2007 | Ambrosio et al. |
| 2007/0219513 | A1 | 9/2007 | Lina et al. |
| 2007/0225663 | A1 | 9/2007 | Watt et al. |
| 2007/0233022 | A1 | 10/2007 | Henley et al. |
| 2008/0011667 | A1 | 1/2008 | Ruschke |
| 2008/0071235 | A1 | 3/2008 | Locke et al. |
| 2008/0082059 | A1 | 4/2008 | Fink et al. |
| 2008/0103462 | A1 | 5/2008 | Wenzel et al. |
| 2008/0132819 | A1 | 6/2008 | Radl et al. |
| 2008/0167593 | A1 | 7/2008 | Fleischmann |
| 2008/0183233 | A1 | 7/2008 | Koch et al. |
| 2008/0200857 | A1 | 8/2008 | Lawhorn |
| 2008/0200906 | A1 | 8/2008 | Sanders et al. |
| 2008/0208147 | A1 | 8/2008 | Argenta et al. |
| 2008/0234641 | A1 | 9/2008 | Locke et al. |
| 2009/0204049 | A1 | 8/2009 | Lee |
| 2010/0207768 | A1 | 8/2010 | Pidgeon et al. |
| 2010/0318071 | A1 | 12/2010 | Wudyka |
| 2011/0112493 | A1 * | 5/2011 | Koch et al. ............ 604/319 |
| 2011/0196321 | A1 | 8/2011 | Wudyka |
| 2011/0288511 | A1 * | 11/2011 | Locke et al. ............ 604/319 |

FOREIGN PATENT DOCUMENTS

| | | |
|---|---|---|
| DE | 295 04 378 U1 | 10/1995 |
| EP | 358 302 | 3/1990 |
| EP | 0 853 950 | 7/1998 |
| EP | 1 088 569 | 4/2001 |
| EP | 1 219 311 | 7/2002 |
| GB | 488 232 | 7/1938 |
| GB | 1 415 096 | 11/1975 |
| GB | 1 549 756 | 3/1977 |
| GB | 2 195 255 A | 4/1988 |
| GB | 2 235 877 A | 3/1991 |
| GB | 2 307 180 A | 5/1997 |
| GB | 2 329 127 A | 3/1999 |
| GB | 2 336 546 A | 10/1999 |
| GB | 2 344 531 A | 6/2000 |
| GB | 2 415 908 | 1/2006 |
| SU | 1762940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1991 |
| WO | WO 92/19313 | 11/1992 |
| WO | WO 93/09727 | 5/1993 |
| WO | WO 94/20041 | 9/1994 |
| WO | WO 96/05873 | 2/1996 |
| WO | WO 97/14450 | 4/1997 |
| WO | WO 00/21586 | 4/2000 |
| WO | WO 03/005943 | 1/2003 |
| WO | WO 03/018098 | 3/2003 |
| WO | WO 03/030966 | 4/2003 |
| WO | WO 03/045492 | 6/2003 |
| WO | WO 03/057070 | 7/2003 |
| WO | WO 03/057071 | 7/2003 |
| WO | WO 03/057307 | 7/2003 |
| WO | WO 03/086232 | 10/2003 |
| WO | WO 03/092620 | 11/2003 |
| WO | WO 03/101508 | 12/2003 |
| WO | WO 2004/018020 | 4/2004 |
| WO | WO 2005/009488 | 2/2005 |
| WO | WO 2006/015599 | 2/2006 |
| WO | WO 2006/105892 | 10/2006 |
| WO | WO 2008/020862 | 2/2008 |
| WO | WO 2008/048481 | 4/2008 |
| WO | WO 2009/004289 | 1/2009 |

OTHER PUBLICATIONS

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

(56) References Cited

OTHER PUBLICATIONS

Bjorn, et al., "Irrigation Treatment in Split-thickness Skin Grafting of Intractable Leg Ulcers," Scand J Plast Reconstr Surg 19: 211-213,1985.
Chardack, et al., "Experimental studies on Synthetic Substitutes for Skin and Their Use in the Treatment of Burns," vol. 155, No. 1 (128-136), 1961.
Chariker, M.E., et al, "Effective Management of Incisional and Cutaneous Fistulae with Closed Suction Wound Drainage," Contemporary Surgery. Jun. 1989, pp. 59-63, vol. 34 USA.
Fleischmann, "Vacuum Sealing for Treatment of Problematical Wounds", University Surgical Clinic and Polyclinic—Accident Surgery Department, WundForum Spezial-IHW 94.
Fleischmann, et al., Vacuum Sealing: Indication, Technique and Results, Emr J Orthop Surg Tramatol (1995) 5:37-40.
Gorica Zivadinovic, et al., "Vacuum Therapy in the Treatment of Peripheral Blood Vessels," Conference Papers of the 5th Timok Medical Days, Majdanpek, 1986 (161-164).
Jeter, Katherine F., et al., "Managing Draining Wounds and Fistulae: New and Established Methods", Chronic Wound Care, 1990, pp. 240-246.
Kostiuchenok, et al., "The Vacuum Effect in the Surgical Treatment of Purulent Wounds," Russian Journal: Vestnik Khirurgii, Sep. 1986, (18-21).
Meyer, MD., et al., "In Surgery, Medicine and the Specialties A Manual of its Practical Application", Bier's Hyperemic Treatment, Second Revised Edition, W.B. Saunders Company, 1909.
Mulder, GD, et al., "Clinicians' Pocket Guide to Chronic Wound Repair," Wound Healing Publications Second Edition, 1991.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (323-326).
Sandén, Göran MD., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Stoll, "Energetic Remedies—Cupping: Healing Within a Vacuum," https:l/www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, "Irrigation Treatment of Leg Ulcers," The Lancet, Sep. 3, 1983 (532-534).
Svedman, et al., "Staphylococcal Wound Infection in the Pig: Part I. Course," Annals of Plastic Surgery, vol. 23, No. 3, Sep. 1989 (212-218).
Teder, et al., "Continuous Wound Irrigation in the Pig," Journal of Investigative Surgery, vol. 3 (399-407).
Usupov, et al., "Active Wound Drainage," Russian Journal: Vestnik Khirugii, Apr. 1987, (42-45).
Yu A. Davydov, et al., "Bacteriological and Cylological Assessment of Vacuum Therapy of Purulent Wounds", Vestnik Khirurgii, Oct. 1988, (48-52).
Yu A. Davydov, et al., "Concepts for Clinical Biological Management of the Wound Process in the Treatment of Purulent Wounds Using Vacuum Therapy," Vestnik Khirurgii, Feb. 1991, 132-135).
Yu A. Davydov, et al., "Vacuum Therapy in the Treatment of Purulent Lactation Mastitis," Russian Journal: Vesnik Khirurgii, Sep. 1986, (66-70).
Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.
Extended European Search Report for Application No. EP 09845932.4 dated Jul. 14, 2014 in five pages.
US 6,216,701, 04/2001, Heaton et al. (withdrawn)
US 7,186,244, 03/2007, Hunt et al. (withdrawn)

* cited by examiner

FLUID COLLECTION CANISTER INCLUDING CANISTER TOP WITH FILTER MEMBRANE AND NEGATIVE PRESSURE WOUND THERAPY SYSTEMS INCLUDING SAME

CROSS-REFERENCE TO RELATED APPLICATIONS

This application is a continuation of U.S. patent application Ser. No. 12/671,995, filed on Feb. 3, 2010, which is a national stage application under 35 U.S.C. §371 of International Patent Application No. PCT/US2009/047137, filed on Jun. 12, 2009, which is a continuation in part of U.S. patent application Ser. No. 12/481,617, filed on Jun. 10, 2009. The disclosures of these prior applications are incorporated by reference in their entireties and are made a part of the present disclosure as if fully set forth herein.

BACKGROUND

1. Technical Field

The present disclosure relates to negative pressure wound therapy systems and, more particularly, to a fluid collection canister including a canister top with a filter membrane and negative pressure wound therapy systems including the same.

2. Discussion of Related Art

Negative pressure therapy, also known as suction or vacuum therapy, has been used in treating and healing wounds. Treating an open wound by applying negative pressure, e.g., reduced or sub-atmospheric pressure, to a localized reservoir over a wound has been found to assist in closing the wound by increasing blood circulation at the wound area, stimulating the formation of granulation tissue and promoting the migration of healthy tissue over the wound. Negative pressure therapy may also inhibit bacterial growth by drawing wound fluids from the wound such as exudate, which may tend to harbor bacteria. Negative pressure therapy can thus be applied as a healing modality for its antiseptic and tissue regeneration effects. This technique has proven effective for treating a variety of wound conditions, including chronic or healing-resistant wounds and ulcers, and is also used for other purposes such as post-operative wound care.

Generally, negative pressure therapy provides for a wound covering to be positioned over the wound to facilitate suction at the wound area. A conduit is introduced through the wound covering to provide fluid communication to an external vacuum source, such as a hospital vacuum system or a portable vacuum pump. Atmospheric gas, wound exudate or other fluids may thus be drawn from the reservoir through the fluid conduit to stimulate healing of the wound. Generally, a fluid collection canister for collecting fluids aspirated from the wound is positioned in the suction line between the wound covering and the vacuum source. Exudate drawn from the reservoir through the fluid conduit may thus be deposited into the collection canister.

During a treatment, vacuum levels within a negative pressure wound therapy system may be monitored and controlled. There are a variety of pressure detecting devices such as pressure gages, switches, transducers and transmitters that can be used for measuring vacuum levels. A negative pressure wound therapy system may not function properly when fluid contamination of various components degrades the capability to accurately measure vacuum levels in the negative pressure wound therapy system. When the collection canister is tilted from upright, fluid may occlude a filter in communication with a pressure detecting device, preventing accurate measurement of vacuum levels in the negative pressure wound therapy system. This may cause the negative pressure wound therapy system to react as if a pneumatic leak is present in the system and may cause vacuum level within the collection canister to go uncontrolled, which may result in improper therapy to the patient.

A mechanism for preventing overfilling of the collection canister may prevent fluid contamination of various components of the negative pressure wound therapy system and help to prevent spillage or leakage of exudate. During a treatment, the collection canister may be prevented from overfilling by a hydrophobic filter at the top of the collection canister that shuts off the air flow to the vacuum source when the collection canister is full. In portable negative pressure wound therapy systems, which may be worn or carried by a patient, there is a likelihood that the apparatus will shift into various orientations while the patient is ambulating, allowing exudate to occlude the filter when the collection canister is not full. Negative pressure therapy may be discontinued or interrupted inadvertently when the filter is occluded during patient ambulation or when the collection canister is tipped over. There is a need for a negative pressure wound therapy system that permits accurate measurement of vacuum levels in the negative pressure wound therapy system and is capable of providing negative pressure therapy for varied orientations of the collection canister.

SUMMARY

The present disclosure relates to a fluid collection canister including a chamber to collect fluids and a canister top disposed over the chamber. The canister top includes a bottom side facing into the chamber, including first and second ribs disposed thereon, a filter membrane attached to the first and second ribs, a first port to communicate with the chamber and a pressure source external to the chamber, and a second port to communicate with the chamber and a sensor external to the chamber. The first port is in fluid communication with a first area, which is bounded by the filter membrane, the first and second ribs and the bottom side of the canister top. The second port is in fluid communication with a second area, which is bounded by the filter membrane, the second rib and the bottom side of the canister top.

The present disclosure also relates to a portable negative pressure wound therapy apparatus including a dressing assembly for positioning over a wound to apply a negative pressure to the wound and a canister assembly in fluid communication with the dressing assembly. The canister assembly includes a control unit, a vacuum source disposed in the control unit, a pressure sensor in communication with the control unit, and a collection canister. The collection canister includes a chamber to collect wound fluids from the dressing assembly, a canister top disposed over the chamber, the canister top including a bottom side facing into the chamber, the bottom side including first and second ribs disposed thereon, an inlet port in fluid communication with the dressing assembly to introduce the wound fluids from the dressing assembly into the chamber, a suction port located on the canister top to communicate with the chamber and the vacuum source, a pressure sensor port located on the canister top to communicate with the chamber and the pressure sensor, and a filter membrane attached to the first and second ribs. The pressure sensor port is in fluid communication with a first chamber, which is bounded by the filter membrane, the first and second ribs and the bottom side of the canister top. The suction port is in fluid communication with a second chamber, which is bounded by the filter membrane, the second rib and the bottom side of the canister top.

BRIEF DESCRIPTION OF THE DRAWINGS

Objects and features of the presently disclosed negative pressure wound therapy systems will become apparent to those of ordinary skill in the art when descriptions of various embodiments thereof are read with reference to the accompanying drawings, of which.

DETAILED DESCRIPTION

Various embodiments of the present disclosure provide negative pressure wound therapy systems (or apparatus) including a collection canister having a chamber to collect wound fluids and a canister top disposed over the chamber. Embodiments of the presently disclosed negative pressure wound therapy systems are generally suitable for use in applying negative pressure to a wound to facilitate healing of the wound in accordance with various treatment modalities. Embodiments of the presently disclosed negative pressure wound therapy systems are entirely portable and may be worn or carried by the user such that the user may be completely ambulatory during the therapy period. Embodiments of the presently disclosed negative pressure wound therapy apparatus and components thereof may be entirely reusable or may be entirely disposable after a predetermined period of use or may be individually disposable whereby some of the components are reused for a subsequent therapy application. Embodiments of the presently disclosed collection canisters interface with a control unit to allow suction from a vacuum source and to allow monitoring of the canister vacuum level.

Hereinafter, embodiments of the presently disclosed negative pressure wound therapy systems will be described with reference to the accompanying drawings. Like reference numerals may refer to similar or identical elements throughout the description of the figures. As it is used in this description, "wound exudate", or, simply, "exudate", generally refers to any fluid output from a wound, e.g., blood, serum, and/or pus, etc. As it is used in this description, "fluid" generally refers to a liquid, a gas or both. As it is used in this description, "pressure" generally refers to positive pressure, negative pressure or both. As it is used in this description, "pressure" is measured relative to the ambient atmospheric pressure. Thus, positive pressure refers to pressure greater than the ambient atmospheric pressure, and negative pressure (or vacuum) refers to pressure less than the ambient atmospheric pressure. As used herein, "transmission line" generally refers to any transmission medium that can be used for the propagation of signals from one point to another.

Figure 1:
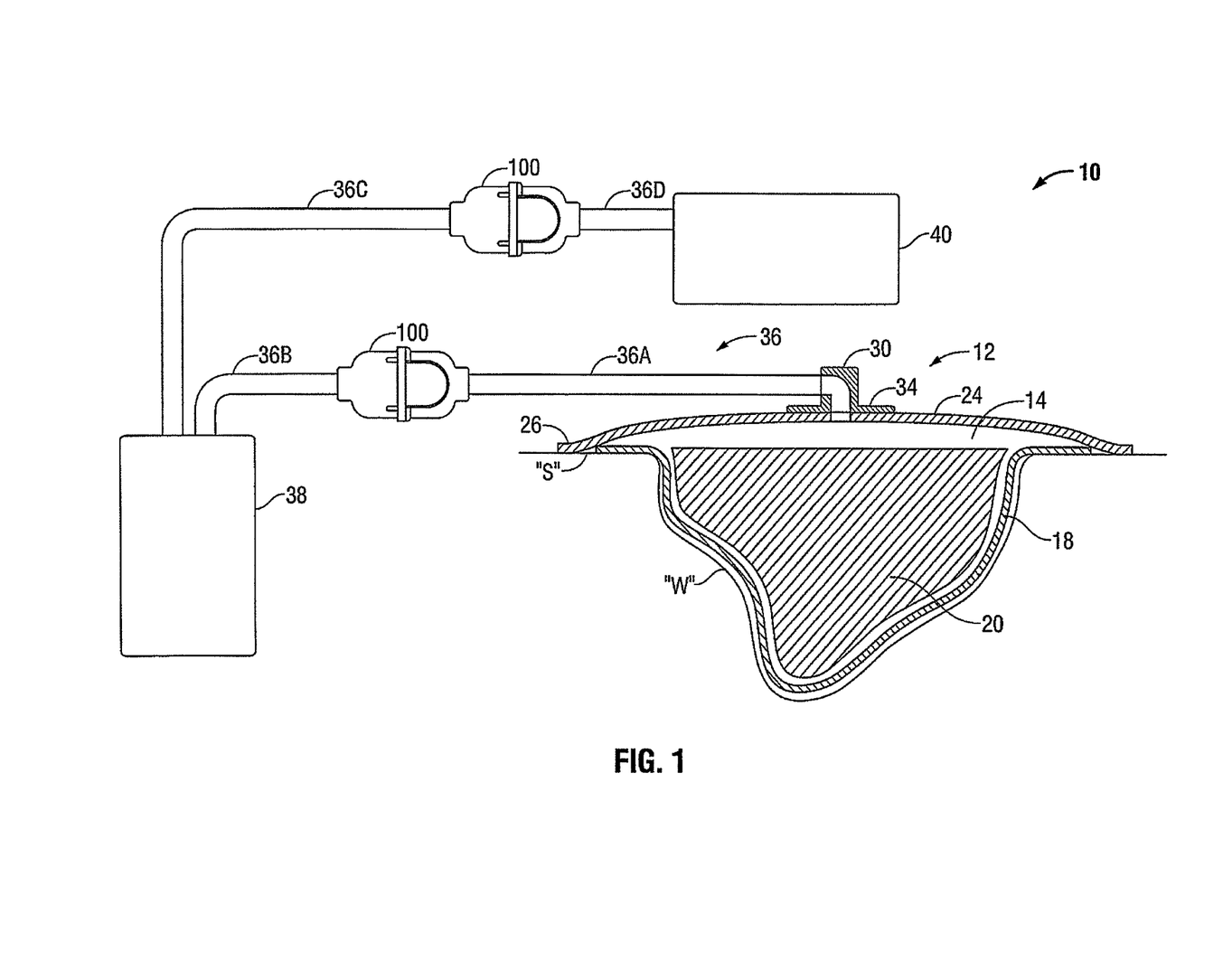
FIG. 1 is a schematic diagram of an embodiment of a negative pressure wound therapy system in accordance with the present disclosure.

Referring to FIG. 1, a negative pressure wound therapy apparatus according to an embodiment of the present disclosure is depicted generally as 10 for use on a wound bed "w" surrounded by healthy skin "s". Negative pressure wound therapy apparatus 10 includes a wound dressing 12 positioned relative to the wound bed "w" to define a vacuum chamber 14 about the wound bed "w" to maintain negative pressure at the wound area. Wound dressing 12 includes a contact layer 18, a wound filler 20 and a wound cover 24.

Contact layer 18 is intended for placement within the wound bed "w" and may be relatively non-supportive or flexible to substantially conform to the topography of the wound bed "w". A variety of materials may be used for the contact layer 18. Contact layer 18 selection may depend on various factors such as the patient's condition, the condition of the periwound skin, the amount of exudate and/or the condition of the wound bed "w". Contact layer 18 may be formed from perforated film material. The porous characteristic of the contact layer 18 permits exudate to pass from the wound bed "w" through the contact layer 18. Passage of wound exudate through the contact layer 18 may be substantially unidirectional such that exudate does not tend to flow back into the wound bed "w". Unidirectional flow may be encouraged by directional apertures, e.g., apertures positioned at peaks of undulations or cone-shaped formations protruding from the contact layer 18. Unidirectional flow may also be encouraged by laminating the contact layer 18 with materials having absorption properties differing from those of the contact layer 18, or by selection of materials that promote directional flow. A non-adherent material may be selected for forming the contact layer 18 such that the contact layer 18 does not tend to cling to the wound bed "w" or surrounding tissue when it is removed. One example of a material that may be suitable for use as a contact layer 18 is commercially available under the trademark XEROFLOW® offered by Tyco Healthcare Group LP (d/b/a Covidien). Another example of a material that may be suitable for use as the contact layer 18 is the commercially available CURITY® non-adherent dressing offered by Tyco Healthcare Group LP (d/b/a Covidien).

Wound filler 20 is positioned in the wound bed "w" over the contact layer 18 and is intended to transfer wound exudate. Wound filler 20 is conformable to assume the shape of any wound bed "w" and may be packed up to any level, e.g., up to the level of healthy skin "s" or to overfill the wound such that wound filler 20 protrudes over healthy skin "s". Wound filler 20 may be treated with agents such as polyhexamethylene biguanide (PHMB) to decrease the incidence of infection and/or other medicaments to promote wound healing. A variety of materials may be used for the wound filler 20. An example of a material that may be suitable for use as the wound filler 20 is the antimicrobial dressing commercially available under the trademark KERLIX™ AMD™ offered by Tyco Healthcare Group LP (d/b/a Covidien).

Cover layer 24 may be formed of a flexible membrane, e.g., a polymeric or elastomeric film, which may include a biocompatible adhesive on at least a portion of the cover layer 24, e.g., at the periphery 26 of the cover layer 24. Alternately, the cover layer 24 may be a substantially rigid member. Cover layer 24 may be positioned over the wound bed "w" such that a substantially continuous band of a biocompatible adhesive at the periphery 26 of the cover layer 24 forms a substantially fluid-tight seal with the surrounding skin "s". An example of a material that may be suitable for use as the cover layer 24 is commercially available under the trademark CURAFORM ISLAND® offered by Tyco Healthcare Group LP (d/b/a Covidien).

Cover layer 24 may act as both a microbial barrier and a fluid barrier to prevent contaminants from entering the wound bed "w" and to help maintain the integrity thereof.

In one embodiment, the cover layer 24 is formed from a moisture vapor permeable membrane, e.g., to promote the exchange of oxygen and moisture between the wound bed "w" and the atmosphere. An example of a membrane that may provide a suitable moisture vapor transmission rate (MVTR) is a transparent membrane commercially available under the trade name POLYSKIN® II offered by Tyco Healthcare Group LP (d/b/a Covidien). A transparent membrane may help to permit a visual assessment of wound conditions to be made without requiring removal of the cover layer 24.

Wound dressing 12 may include a vacuum port 30 having a flange 34 to facilitate connection of the vacuum chamber 14 to a vacuum system. Vacuum port 30 may be configured as a rigid or flexible, low-profile component and may be adapted to receive a conduit 36 in a releasable and fluid-tight manner. An adhesive on at least a portion of the underside of the flange 34 may be used to provide a mechanism for affixing the vacuum port 30 to the cover layer 24. The relative positions, size and/or shape of the vacuum port 30 and the flange 34 may be varied from an embodiment depicted in FIG. 1. For example, the flange 34 may be positioned within the vacuum chamber 14 such that an adhesive on at least a portion of an upper side surface of the flange 34 affixes the vacuum port 30 to the cover layer 24. A hollow interior portion of the vacuum port 30 provides fluid communication between the conduit 36 and the vacuum chamber 14. Conduit 36 extends from the vacuum port 30 to provide fluid communication between the vacuum chamber 14 and the vacuum source 40. Alternately, the vacuum port 30 may not be included in the dressing 12 if other provisions are made for providing fluid communication with the conduit 36.

Any suitable conduit may be used for the conduit 36, including conduit fabricated from flexible elastomeric or polymeric materials. In the negative pressure wound therapy apparatus 10 illustrated in FIG. 1, the conduit 36 includes a first conduit section 36A, a second conduit section 36B, a third conduit section 36C and a fourth conduit section 36D. The first conduit section 36A extends from the vacuum port 30 and is coupled via a fluid line coupling 100 to the second conduit section 36B, which extends to the collection canister 38. The third conduit section 36C extends from the collection canister 38 and is coupled via another fluid line coupling 100 to the fourth conduit section 36D, which extends to the vacuum source 40. The shape, size and/or number of conduit sections of the conduit 36 may be varied from the first, second, third and fourth conduit sections 36A, 36B, 36C and 36D depicted in FIG. 1.

The first, second, third and fourth conduit sections 36A, 36B, 36C and 36D of the conduit 36 may be connected to components of the apparatus 10 by conventional air-tight means, such as, for example, friction fit, bayonet coupling, or barbed connectors. The connections may be made permanent. Alternately, a quick-disconnect or other releasable connection means may be used to provide some adjustment flexibility to the apparatus 10.

Collection canister 38 may be formed of any type of container that is suitable for containing wound fluids. For example, a semi-rigid plastic bottle may be used for the collection canister 38. A flexible polymeric pouch or other hollow container body may be used for the collection canister 38. Collection canister 38 may contain an absorbent material to consolidate or contain the wound fluids or debris. For example, super absorbent polymers (SAP), silica gel, sodium polyacrylate, potassium polyacrylamide or related compounds may be provided within collection canister 38. At least a portion of canister 38 may be transparent or semi-transparent, e.g., to permit a visual assessment of the wound exudate to assist in evaluating the color, quality and/or quantity of exudate. A transparent or semi-transparent portion of the collection canister 38 may permit a visual assessment to assist in determining the remaining capacity or open volume of the canister and/or may assist in determining whether to replace the collection canister 38.

The collection canister 38 is in fluid communication with the wound dressing 12 via the first and second conduit sections 36A, 36B. The third and fourth conduit sections 36C, 36D connect the collection canister 38 to the vacuum source 40 that generates or otherwise provides a negative pressure to the collection canister 38. Vacuum source 40 may include a peristaltic pump, a diaphragmatic pump or other suitable mechanism. Vacuum source 40 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg to about 125 mmHg, or about 40 mmHg to about 80 mmHg. One example of a peristaltic pump that may be used as the vacuum source 40 is the commercially available Kangaroo PET Eternal Feeding Pump offered by Tyco Healthcare Group LP (d/b/a Covidien). Vacuum source 40 may be actuated by an actuator (not shown) which may be any means known by those skilled in the art, including, for example, alternating current (AC) motors, direct current (DC) motors, voice coil actuators, solenoids, and the like. The actuator may be incorporated within the vacuum source 40.

In embodiments, the negative pressure wound therapy apparatus 10 includes one or more fluid line couplings 100 that allow for selectable coupling and decoupling of conduit sections. For example, a fluid line coupling 100 may be used to maintain fluid communication between the first and second conduit sections 36A, 36B when engaged, and may interrupt fluid flow between the first and second conduit sections 36A, 36B when disengaged. Thus, fluid line coupling 100 may facilitate the connection, disconnection or maintenance of components of the negative pressure wound therapy apparatus 10, including the replacement of the collection canister 38. Additional or alternate placement of one or more fluid line couplings 100 at any location in line with the conduit 36 may facilitate other procedures. For example, the placement of a fluid line coupling 100 between the third and fourth conduit sections 36C, 36D, as depicted in FIG. 1, may facilitate servicing of the vacuum source 40.

Figure 2:
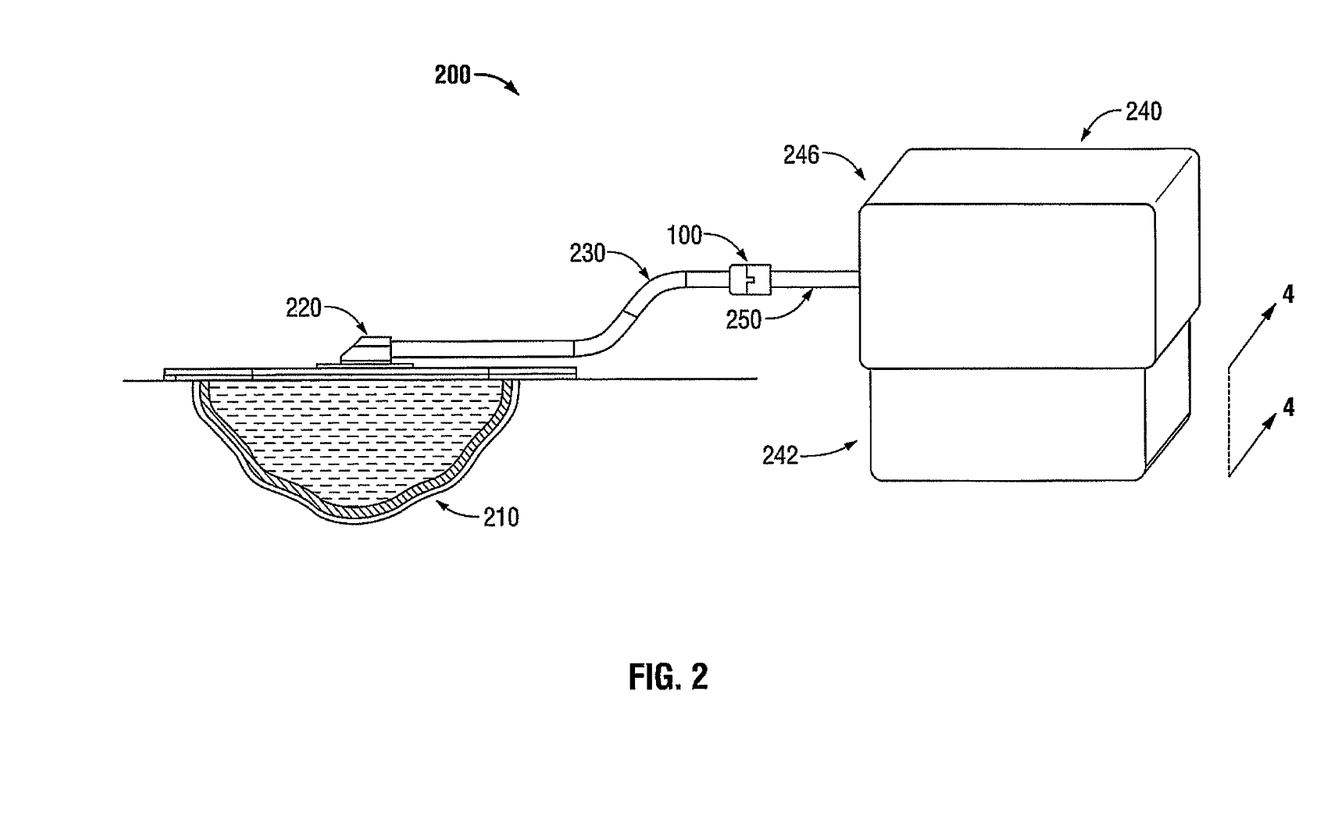
FIG. 2 is a schematic diagram of an embodiment of a negative pressure wound therapy system including a canister assembly in accordance with the present disclosure.

Referring to FIG. 2, the negative pressure wound therapy system shown generally as 200 includes a dressing assembly 210, a wound port assembly 220, an extension assembly 230 and a canister assembly 240. Dressing assembly 210 is positioned relative to the wound area to define a vacuum chamber about the wound area to maintain negative pressure at the wound area. Dressing assembly 210 may be substantially sealed from extraneous air leakage, e.g., using adhesive coverings. Wound port assembly 220 is mounted to the dressing assembly 210. For example, wound port assembly 220 may include a substantially continuous band of adhesive at its periphery for affixing the wound port assembly 220 to the dressing assembly 210. Extension assembly 230 is coupled between the wound port assembly 220 and the canister assembly 240 and defines a fluid flow path between the wound port assembly 220 and the canister assembly 240. A hollow interior of the wound port assembly 220 provides fluid communication between the extension assembly 230 and the interior of the dressing assembly 210. Dressing assembly 210 and the wound port assembly 220 shown in FIG. 2 are similar to components of the wound dressing 12 of FIG. 1 and further description thereof is omitted in the interests of brevity.

Canister assembly 240 includes a control unit 246 and a collection canister 242 disposed below the control unit 246. Control unit 246 and the collection canister 242 may be releasably coupled. Mechanisms for selective coupling and decoupling of the control unit 246 and the collection canister 242 include fasteners, latches, clips, straps, bayonet mounts, magnetic couplings, and other devices. Collection canister 242 may include any container suitable for containing wound fluids. In embodiments, the canister assembly 240 is configured to substantially prevent escape of exudate into the user's immediate environment when the collection canister 242 is decoupled from the control unit 246.

In one embodiment, the negative pressure wound therapy system 200 is capable of operating in a continuous mode or an alternating mode. In the continuous mode, the control unit 246 controls a pump (e.g., suction pump 360 shown in FIG. 3) to continuously supply a selected vacuum level at the collection canister 242 to create a reduced pressure state within the dressing assembly 210. In the alternating mode, the control unit 246 controls the pump to alternatingly supply a first negative pressure, e.g., about 80 mmHg, at the collection canister 242 for a preset fixed amount of time and a second negative pressure, e.g., about 50 mmHg, at the collection canister 242 for a different preset fixed amount of time.

In general, the output of the pump is directly related to the degree of air leakage in the negative pressure wound therapy system 200 and the open volume in the collection canister 242. If there is sufficient air leakage in the system 200, e.g., at the dressing assembly 210, the pump can remain on continuously and the control unit 246 can control negative pressure at the collection canister 242 by adjusting the pump speed. Alternatively, if there is not sufficient air leakage in the system 200 to permit the pump to remain on continuously, the control unit 246 can control negative pressure at the collection canister 242 by turning the pump on and off, e.g., for non-equal on/off periods of time.

Control unit 246 responds to various sensed events by signaling alarms. Various types of conditions may be signaled by alarms. In embodiments, control unit 246 is capable of signaling alarms for failed pressure sensor condition, use odometer expired condition, watchdog reset condition, failed pump condition, leak condition, replace canister condition, excessive vacuum condition, failed LEDs condition, low battery condition, very low battery condition, and failed battery condition. Priority levels may be associated with alarms. In embodiments, the priority levels of alarms are low priority alarm, medium priority alarm, and system alarm (highest priority). Low priority alarms, when triggered, may be continuously indicated. Medium priority alarms and system alarms, when triggered, may have a flashing indication.

Control unit 246 may stop operation of the pump (e.g., suction pump 360 shown in FIG. 3) in response to an alarm, e.g., depending on alarm type and/or priority level. In embodiments, the control unit 246 stops operation of the pump in response to system alarms, e.g., failed pressure sensor system alarm, use odometer expired system alarm, watchdog reset system alarm, failed pump system alarm, excessive vacuum system alarm, and/or failed LEDs system alarm.

If an air leak develops in the negative pressure wound therapy system 200, e.g., at the dressing assembly 210, for which the control unit 246 cannot compensate by increasing the pump speed, the control unit 246 may indicate an alarm. For example, the control unit 246 may indicate a leak alarm after two consecutive minutes of operation in which the vacuum level is below the current set point (or below the minimum level of a set point range).

Audible indicatory means may also be incorporated or associated with the control unit 246 to notify the user of a condition, e.g., leak, canister assembly tip, failed pressure sensor, failed pump, excessive vacuum, or low battery conditions. The audio indication for some alarm types can be paused by pressing a pause alarm button (not shown).

In embodiments, the control unit 246 includes a user interface (not shown). Control unit 246 also includes a processor (e.g., 310 shown in FIG. 3). A pressure sensor (e.g., 340 shown in FIG. 3) is electrically coupled to the processor. The user turns ON the canister assembly 240 by pressing a power button (not shown). When the power button is pressed, the control unit 246 performs a series of internal checks during power up. In one embodiment, after successfully completing the power-up tasks, the control unit 246 turns on the pump 360 using the stored settings. At initial activation of the canister assembly 240, the stored settings are the default settings. In one embodiment, the default settings for controlling the pump 360 are 80 mmHg and continuous mode. In one embodiment, the currently stored vacuum level setting can be altered by the user, e.g., to 50 mmHg. In one embodiment, the currently stored mode setting can be altered by the user, e.g., to an alternating mode.

Canister assembly 240 may be constructed from a variety of materials such as Lucite™ polycarbonate, metals, metal alloys, plastics, or other durable materials capable of withstanding forces applied during normal use, and may have some capability of withstanding possibly excessive forces resulting from misuse. Collection canister 242 may include a window (not shown) with fluid level markings or graduations for promoting visual assessment of the amount of exudate contained within the collection canister 242. A transparent or partially transparent collection canister 242 may thus assist in determining the remaining capacity of the collection canister 242 and/or when the collection canister 242 should be replaced.

Figure 3:
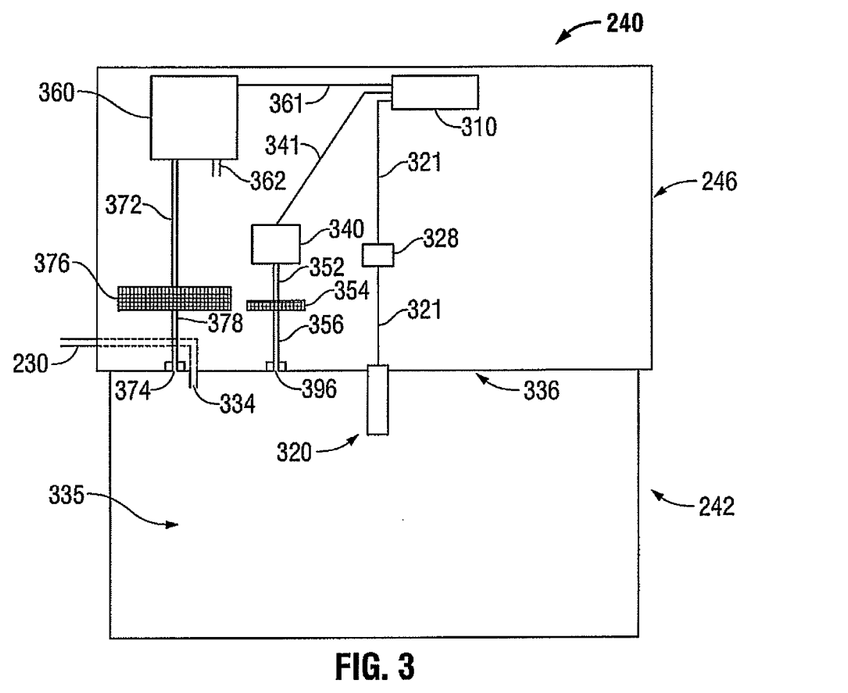
FIG. 3 is a schematic diagram of the canister assembly of the negative pressure wound therapy system illustrated in FIG. 2.

Referring to FIG. 3, an embodiment of the canister assembly 240 illustrated in FIG. 2 is shown and includes a control unit 246 and a collection canister 242. In embodiments, the canister assembly 240 is coupled via an extension assembly 230 to a dressing assembly (e.g., 12 shown in FIG. 1) to apply negative pressure to a wound to facilitate healing of the wound in accordance with various treatment modalities.

Collection canister 242 includes a chamber 335 to collect wound fluids from the dressing assembly, a canister top 336 disposed over the chamber, a suction port 374 to communicate with the chamber 335 and the suction pump 360, a canister inlet port 334 to introduce the wound fluids from the dressing assembly into the chamber 335, and a pressure sensor port 396 to communicate with the chamber 335 and the pressure sensor 340. Suction port 374 may include an o-ring on the outside diameter to provide for appropriate sealing to the suction port when the collection canister 242 and control unit 246 are attached together. Collection canister 242 may be disposable. Collection canister 242 may contain a liner that is disposable.

In embodiments, the canister inlet port 334 is coupled to the extension assembly 230. Canister inlet port 334 may be connectable with the extension assembly 230 by conventional air and fluid tight means. In embodiments, the canister inlet port 334 may contain a luer lock or other connector within the purview of those skilled in the art to secure the end of the extension assembly 230 with the canister inlet port 334. Canister inlet port 334 may be configured to receive a cap for use to prevent leakage of exudate and odor from the chamber 335 when the collection canister 242 is separated from the control unit 246. In alternate embodiments, the canister inlet port 334 is coupled to a canister inlet conduit (e.g., 250 shown in FIG. 2) in fluid communication with the dressing assembly.

In embodiments, the control unit 246 includes a suction pump 360, a pump inlet conduit 372, a pump outlet conduit 362, a pressure sensor 340, and a pressure sensor conduit 352. Additionally, a first filter element 376 and/or a second filter element 354 may be included. A first connecting channel 378 may be included to provide fluid communication between the first filter element 376 and the suction port 374 located on the canister top 336. A second connecting channel 356 may be included to provide fluid communication between the second filter element 354 and the pressure sensor port 396 located on the canister top 336.

Suction pump 360 may provide negative pressure produced by a piston drawn through a cylinder. Suction pump 360 may be a peristaltic pump or a diaphragm pump. Suction pump 360 may be a manual pump or an automated pump. The automated pump may be in the form of a portable pump, e.g., a small or miniature pump that maintains or draws adequate and therapeutic vacuum levels. In one embodiment, the suction pump 360 is a portable, lightweight, battery-operated, DC motor-driven pump. A vibration damping tape (not shown), e.g., visco-elastic damping tape, may be applied to the outer surface of the suction pump 360 to reduce vibration and its associated noise. Suction pump 360 may be contained within its own sub-housing (not shown), which may be formed substantially entirely of molded foam, e.g., used as a silencer to provide sound mitigation by reducing the sound energy of the expelled air during operation of the suction pump 360, and may include a carbon loaded foam. Suction pump 360 provides negative pressure within the chamber 335 of the collection canister 242 by drawing air through the suction port 374. Exhaust air from the suction pump 360 is vented through an exhaust port (not shown) via the pump outlet conduit 362. Pump outlet conduit 362 may be coupled to one or more filters (not shown) for filtering the exhaust air from the pump 360.

In embodiments, the pump inlet conduit 372 provides fluid communication between the suction pump 360 and the suction port 374 located on the canister top 336, when the control unit 246 and the collection canister 242 are operably coupled to each other. In alternate embodiments, first filter element 376 is disposed between the suction pump 360 and the suction port 374. Pump inlet conduit 372 may be adapted to provide fluid communication between the suction pump 360 and the first filter element 376. First filter element 376 may include one or more filters and is configured to substantially prevent entry of exudate into the suction pump 360. In embodiments, the control unit 246 stops operation of the suction pump 360 when the first filter element 376 becomes occluded. A variety of filters can be used for the first filter element 376. In one embodiment, the first filter element 376 includes a hydrophobic filter that substantially prevents fluids from entering into the suction pump 360 and potentially causing damage to electronics or pneumatic components.

Pressure sensor 340 is in fluid communication with the collection canister 242 to detect the vacuum level within the chamber 335 of the collection canister 242. In embodiments, the pressure sensor 340 generates an electrical signal that varies as a function of vacuum level within the chamber 335, and the signal is communicated to the processor 310. Logic associated with the pressure sensor 340 and the pump 360 may reduce the speed of the pump 360 or stop operation of the pump 360 in response to the vacuum level detected by the pressure sensor 340. Any suitable device capable of detecting pressure may be utilized for the pressure sensor 340, including, but not limited to, a pressure switch or a pressure transducer or transmitter:

In embodiments, the pressure sensor conduit 352 provides fluid communication between the pressure sensor 340 and the pressure sensor port 396 located on the canister top 336, when the control unit 246 and the collection canister 242 are operablely coupled to each other. In alternate embodiments, second filter element 354 is disposed between the pressure sensor 340 and the pressure sensor port 396. Pressure sensor conduit 352 may be adapted to provide fluid communication between the pressure sensor 340 and the second filter element 354. Second filter element 354 may include one or more filters and is configured to substantially prevent entry of exudate into the pressure sensor 340. A variety of filters can be used for the second filter element 354. In one embodiment, the second filter element 354 includes a hydrophobic filter that substantially prevents fluid contamination of the pressure sensor 340.

In embodiments, the first connecting channel 378 provides fluid communication between the first filter element 376 and the suction port 374, when the control unit 246 and the collection canister 242 are operably coupled to each other. First connecting channel 378 may be coupled to a control suction port (not shown) located on the bottom side of the control unit 246 and configured to engage with the suction port 374 located on the canister top 336 when the control unit 246 and the collection canister 242 are joined together. In embodiments, the second connecting channel 356 provides fluid communication between the second filter element 354 and the pressure sensor port 396, when the control unit 246 and the collection canister 242 are operably coupled to each other. Second connecting channel 356 may be coupled to a control unit pressure sensor port (not shown) located on the bottom side of the control unit 246 and configured to engage with the pressure sensor port 396 located on the canister top 336 when the control unit 246 and the collection canister 242 are joined together.

Control unit 246 also includes a processor 310. In embodiments, the processor 310 is electrically coupled via a transmission line 341 to the pressure sensor 340 and electrically coupled via a transmission line 361 to the suction pump 360. Processor 310 may include any type of computing device, computational circuit, or any type of processor or processing circuit capable of executing a series of instructions that are stored in a memory (not shown) of the control unit 246. The series of instructions may be transmitted via propagated signals for execution by processor 310 for performing the functions described herein and to achieve a technical effect in accordance with the present disclosure. Control unit 246 may also include a user interface (not shown).

Canister assembly 240 may also include a sensor 320. In embodiments, the sensor 320 is used to measure resistance, capacitance or voltage to provide feedback to the processor 310 indicative of a condition. In embodiments, an electric circuit 328 is electrically coupled via a transmission line 321 between the sensor 320 and the processor 310. Electric circuit 328 is configured to detect an electrical property associated with the sensor 320 and may include various components. Although the electric circuit 328 is shown as a separate circuit in FIG. 3, it may be incorporated into the sensor 320, the processor 310, or other component, e.g., a printed circuit board (not shown) associated with the processor 310.

Figure 4:
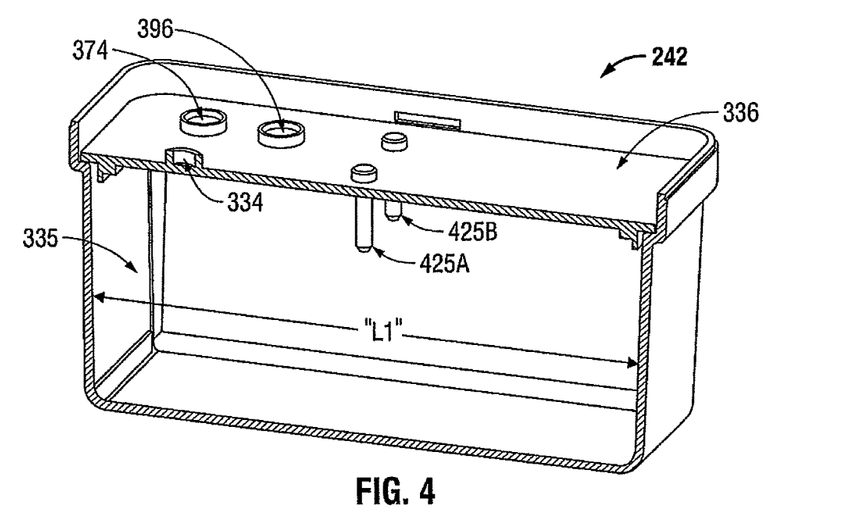
FIG. 4 is a cross-sectional view of the collection canister of the canister assembly shown in FIG. 2 taken along the lines 4-4.

Sensor 320 may include an electrode pair (e.g., 425A, 425B shown in FIG. 4). Sensor 320 may include multiple electrode pairs. In embodiments, any change in the resistance, capacitance or voltage feedback occurring when the electrodes are simultaneously in contact with exudate in the collection canister 242 is used to indicate a replace-collection-canister condition or a full-collection-canister condition (described later in this disclosure). Examples of sensor and electric circuit embodiments are disclosed in commonly assigned U.S. patent application No. 12/471,789 filed on May 26, 2009 and issued as U.S. Pat. No. 8,827,983 on Sep. 9 2014, entitled "SENSOR WITH ELECTRICAL CONTACT PROTECTION FOR USE IN FLUID COLLECTION CANISTER AND NEGATIVE PRESSURE WOUND THERAPY SYSTEMS INCLUDING SAME", the disclosure of which is herein incorporated by reference in its entirety.

Referring to FIG. 4, an embodiment of the collection canister 242 of the canister assembly 240 illustrated in FIG. 3 is shown and includes the canister top 336, the chamber 335, which has length "L1", the canister inlet port 334, the suction port 374, and the pressure sensor port 396. The sensor 320 of FIG. 3 is shown as an electrode pair 425A, 425B in FIG. 4. In embodiments, an electric potential (or voltage) is applied to the electrodes 425A, 425B. When a voltage is supplied and the electrodes 425A, 425B are simultaneously in contact with an ionic fluid, e.g., exudate, electric current flows via an electro-chemical reaction that occurs between the ions in the fluid and the electrically polarized electrodes 425A, 425B.

In embodiments, one or more electrode pairs (e.g., 425A, 425B shown in FIG. 4) is coupled to an electric circuit (e.g., 328 shown in FIG. 3), which is configured to detect an electrical properly associated with the electrode pair(s). In embodiments, a measurement of the change in voltage across the electrode pair(s) as a result from the flow of current is used to activate an indicator (not shown) as notification to the user of a condition. For example, an indicator may be activated to notify the user that the collection canister 242 is full, which may be referred to as the full-collection-canister condition. An indicator may be activated to notify the user that it is time to replace the collection canister 242, which may be referred to as the replace-collection-canister condition. The occurrence of a replace-collection-canister condition indicates that a volume of exudate (generally being less than the volume of the chamber 355) has been collected. User notification of a replace-collection-canister condition may thus provide some flexibility to the user in the timing of the replacement or emptying of the collection canister 242, by allowing an additional time period of operation before the volume of the collected exudate reaches the maximum volume capacity of the chamber 355.

Figure 5:
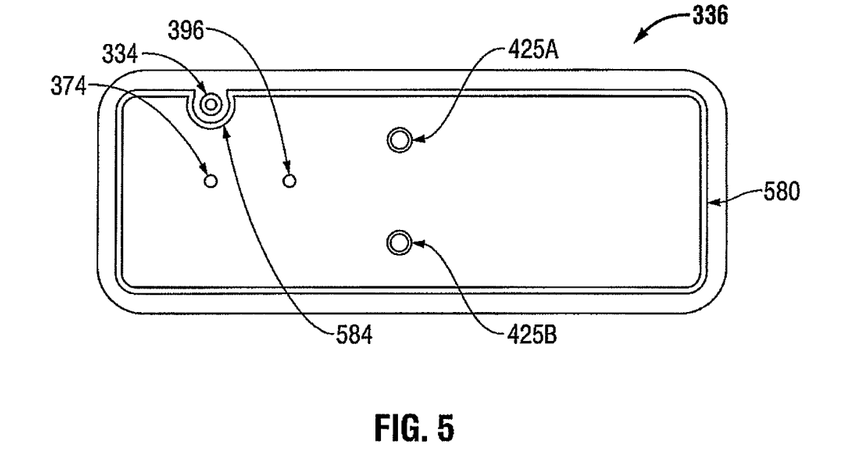
FIG. 5 is a bottom view of the canister top of the collection canister shown in FIG. 4.

Referring to FIG. 5, the bottom side of the canister top 336 illustrated in FIG. 4 is shown and includes the canister inlet port 334, the suction port 374, the pressure sensor port 396 and the two electrodes 425A, 425B. Additionally, a side wall 580 with a recessed portion 584 is included. In embodiments, the suction port 374, the pressure sensor port 396 and the two electrodes 425A, 425B are disposed to the interior of the side wall 580. Side wall 580 is adapted to provide engagement of the canister top 336 with the upper end of the peripheral wall of the chamber 335 and may help to provide sealing of the canister top with the chamber 335. In one embodiment, the peripheral edge of the recess portion 584 is shaped to partly encircle the canister inlet port 334. The relative positions, size and/or shape of the side wall 580, the canister inlet port 334, the suction port 374, the pressure sensor port 396 and the two electrodes 425A, 425B may be varied from an embodiment depicted in FIG. 5.

Canister top 336 may be fabricated from plastic materials by molding techniques. Canister top 336 may be secured to the open top of the collection canister 242 by friction fit between the side wall 580 and the peripheral wall of the chamber 335. Side wall 580 may be fixably attached to the upper end of the peripheral wall of the chamber 335, e.g., using an ultrasonic welding process.

Figure 6:
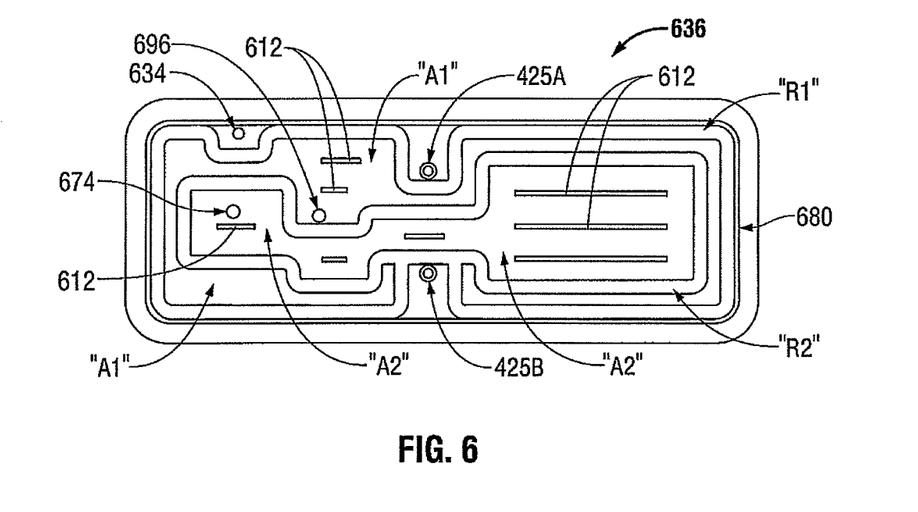
FIG. 6 is a schematic diagram of another embodiment of a canister top of a collection canister in accordance with the present disclosure.
Figure 7:
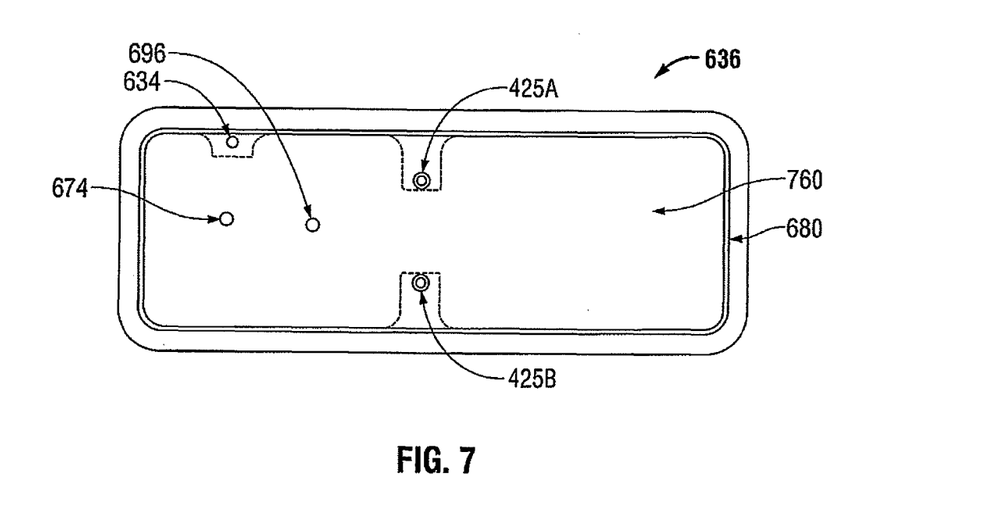
FIG. 7 is a schematic diagram of the canister top illustrated in FIG. 6, shown with a filter membrane, in accordance with the present disclosure.
Figure 8:
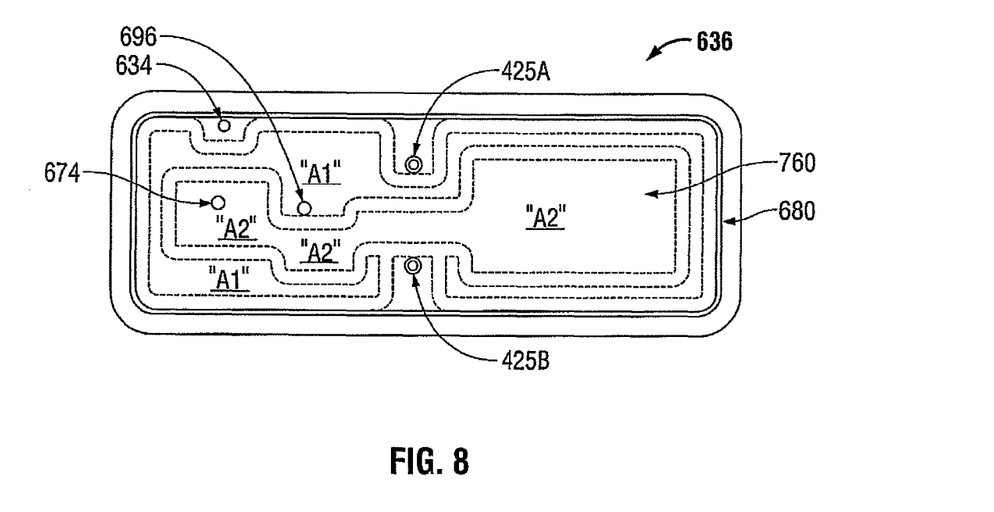
FIG. 8 is a schematic diagram of the canister top illustrated in FIG. 7 with the outer sealing rib and the isolating rib of FIG. 6 shown in phantom.

In FIGS. 6 through 8, another embodiment of a canister top of a collection canister (e.g., 242 shown in FIG. 3) is shown. Canister top 636 includes a canister inlet port 634, a suction port 674 and a pressure sensor port 696. In embodiments, the canister top 636 may also include one or more electrode pairs, e.g., electrode pair 425A, 425B, as described above. Canister top 636 includes a side wall 680, an outer sealing rib "R1" and an isolating rib "R2". In embodiments, the canister top 636 may include support elements 612 that are configured to provide support for a filter membrane (e.g., 760 shown in FIG. 7).

As shown in FIGS. 6 and 8, the outer sealing rib "R1" and the isolating rib "R2" define two chambers, "A1" and "A2", which are pneumatically isolated from each other by the isolating rib "R2". In embodiments, the first chamber "A1" includes the pressure sensor port 696 and the second chamber "A2" includes the suction port 674. In alternate embodiments, the first chamber "A1" includes the suction port 674 and the second chamber "A2" includes the pressure sensor port 696. Although the sensor port 696 and the suction port 674 are shown and described as included in pneumatically isolated chambers, it is contemplated herein that the pressure sensor port 696 and the suction port 674 may be included in same chamber.

In embodiments, the exterior wall of the outer sealing rib "R1", or portion thereof, is disposed directly adjacent to or substantially adjacent to the side wall 680. In embodiments, the isolating rib "R2", or portion thereof, is spaced apart from the interior wall of the outer sealing rib "R1". In the illustrated embodiment, the first chamber "A1" is an elongated pathway that extends approximately around the perimeter of the canister top and is formed between the isolating rib "R2" and the outer sealing rib "R1". Although the first chamber "A1" is shown and described as an elongated pathway including the pressure sensor port 696, it is contemplated herein that the first chamber "A1" may include multiple pathways in fluid communication with the pressure sensor port 696.

Referring to FIG. 7, the canister top 636 of FIG. 6 is shown and includes a filter membrane 760 disposed to the interior of the side wall 680. Filter membrane 760 may include a micro-pore filter membrane. In embodiments, the filter membrane 760 is cut to the profile of the outer sealing rib "R1". Filter membrane 760 is attached to the isolating rib "R2" and the outer sealing rib "R1" and may be attached to the support elements 612. Filter membrane 760 may be attached to the outer sealing rib "R1" and the isolating rib "R2" by adhesive such as UV cure, catalyzed, vulcanized or other type, or welded by ultrasonic or radio frequency means.

Filter membrane 760 generally allows air flow while substantially preventing liquid and bacterial passage therethrough. In embodiments, the filter membrane 760 allows air flow to the suction pump (e.g., 360 shown in FIG. 3) and allows the vacuum level at the collection canister to be monitored using a pressure sensor (e.g., 340 shown in FIG. 3) in fluid communication with the collection canister through the filter membrane 760. Negative pressure wound therapy systems including a collection canister having a canister top in accordance with embodiments of the present disclosure may be capable of accurate measurement of vacuum levels within the collection canister and capable of providing negative pressure therapy for varied orientations of the collection canister.

Figure 9:
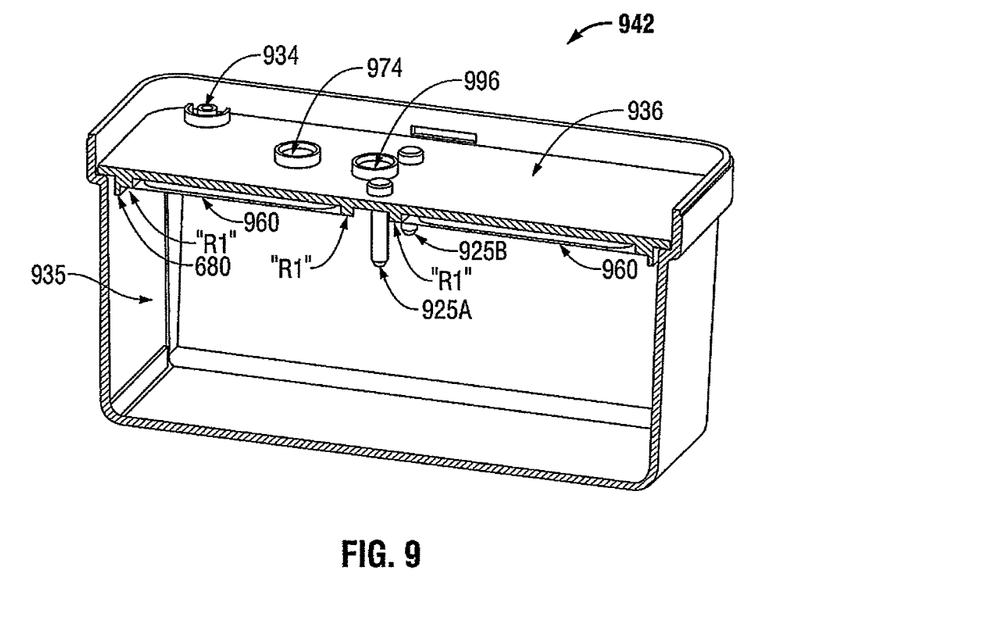
FIG. 9 is a cross-sectional view of another embodiment of a collection canister in accordance with the present disclosure.

Referring to FIG. 9, another embodiment of a collection canister 942 is shown and includes a chamber 935 to collect fluids and a canister top 936 disposed over the chamber 935. The canister top 936 includes a bottom side facing into the chamber 935. The bottom side of the canister top 936 includes first and second ribs, "R1" and "R2", disposed thereon, and a side wall 680, as described above. A filter membrane 960 is attached to the first and second ribs, "R1" and "R2". Canister top 936 also includes a first port 974 to communicate with the chamber 935 and a pressure source external to the chamber, and a second port to communicate with the chamber 935 and a sensor external to the chamber 935. The first port is in fluid communication with a first area "A1", which is bounded by the filter membrane 960, the first and second ribs, "R1" and "R2", and the bottom side of the canister top 936. The second port is in fluid communication with a second area "A2", which is bounded by the filter membrane 960, the second rib "R2" and the bottom side of the canister top 936. In embodiments, the canister top 936 also includes a third port 934 to introduce the fluids into the chamber 935.

Figure 10:
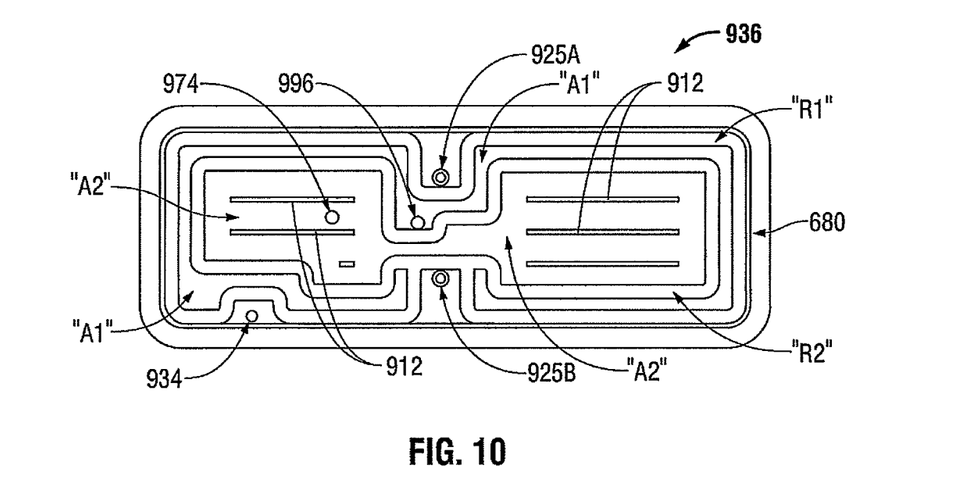
FIG. 10 a bottom view of the canister top of the collection canister shown in FIG. 9.
Figure 11:
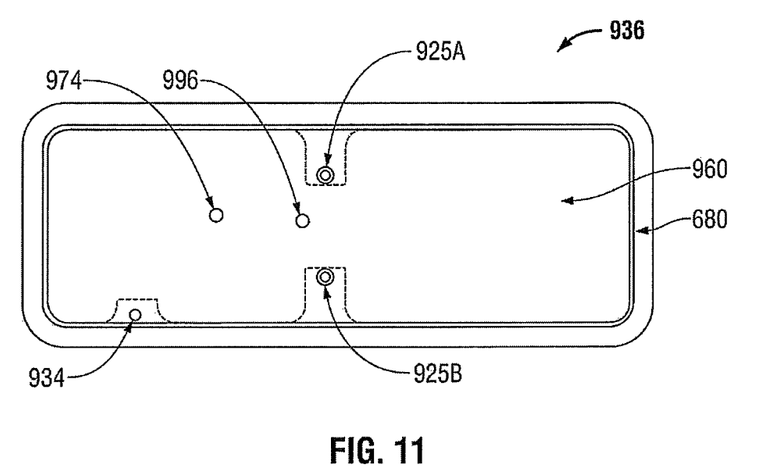
FIG. 11 is a schematic diagram of the canister top illustrated in FIG. 10, shown with a filter membrane, in accordance with the present disclosure.
Figure 12:
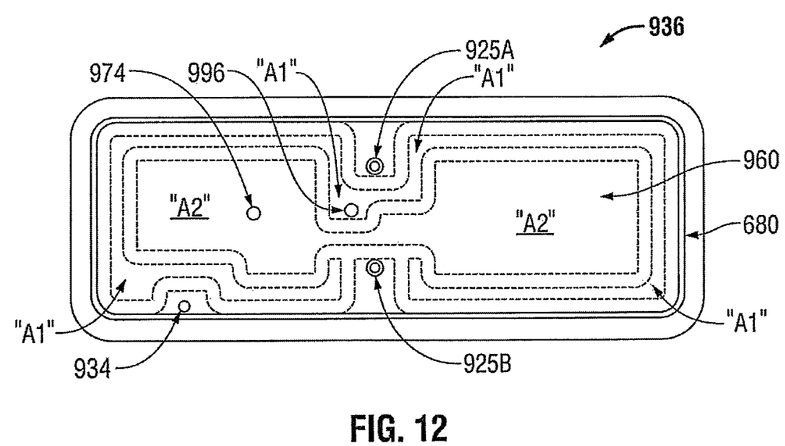
FIG. 12 is a schematic diagram of the canister top illustrated in FIG. 11 with the outer sealing rib and the isolating rib of FIG. 10 shown in phantom.

Referring to FIGS. 10 through 12, the canister top 936 of the collection canister 942 of FIG. 9 is shown. Canister top 936 includes the side wall 680 shown in FIGS. 6 through 8. Canister top 936 includes a first port 974 and a second port 996 and may include a third port 934, as described above. In embodiments, the canister top 936 may include one or more electrode pairs, e.g., electrode pair 925A, 925B. Electrode pair 925A, 925B shown in FIG. 9 is substantially similar to the electrode pair 425A, 425B of the collection canister 242 illustrated in FIG. 4 and further description thereof is omitted in the interests of brevity.

Canister top 936 also includes a first rib "R1" and a second rib "R2". As shown in FIGS. 10 and 12, the first rib "R1" and the second rib "R2" define two areas, "A1" and "A2", which are pneumatically isolated from each other by the second rib "R2". As shown in FIG. 11, the filter membrane 960 is cut to the profile of the first rib "R1". Filter membrane 960 may include any suitable material capable of allowing air flow while substantially preventing liquid and bacterial passage therethrough. Filter membrane 960 may include a micro-pore filter membrane. In embodiments, the canister top 936 may include support elements 912 that are configured to provide support for the filter membrane 960. In embodiments, the filter membrane 960 is attached to the first rib "R1" and the second rib "R2" and may be attached to the support elements 912. The relative positions, size and/or shape of the first rib "R1", the second rib "R2" and the support elements 912 may be varied from an embodiment depicted in FIGS. 10 through 12.

Although embodiments of the present disclosure have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A fluid collection canister, comprising:
   a chamber configured to collect fluids;
   a canister top disposed over the chamber, the canister top comprising a bottom side facing into the chamber, the bottom side including first and second ribs disposed thereon;
   a filter membrane configured to be attached to the first and second ribs,
   a first port located on the canister top, the first port configured to communicate with the chamber and a pressure source external to the chamber;
   a second port located on the canister top, the second port configured to communicate with the chamber and a pressure sensor external to the chamber; and
   a third port located on the canister, the third port configured to communicate with the chamber and to introduce the fluids into the chamber,
   wherein the first port is in fluid communication with a first area, the first area bounded by the filter membrane, the first and second ribs and the bottom side of the canister top,
   wherein the second port is in fluid communication with a second area, the second area bounded by the filter membrane, the second rib and the bottom side of the canister top, and
   wherein the first area and the second area are isolated from each other by the second rib.

2. The fluid collection canister of claim 1, wherein the filter membrane is cut to a profile of the first rib.

3. The fluid collection canister of claim 1, wherein the filter membrane includes a micro-pore filter membrane.

4. The fluid collection canister of claim 1, wherein the first and second areas are pneumatically isolated from each other by the second rib.

5. The fluid collection canister of claim 1, further comprising a side wall to provide engagement of the canister top with an upper end of a peripheral wall of the chamber.

6. The fluid collection canister of claim 5, wherein at least a portion of the first rib is disposed adjacent to the side wall.

7. The fluid collection canister of claim 1, wherein the collection canister is configured to be in fluid communication with a control unit, wherein the pressure source is disposed in the control unit and the pressure sensor is configured to be in communication with the control unit.

8. The fluid collection canister of claim 7, wherein the control unit monitors and controls a negative pressure within the collection canister.

* * * * *